(12) United States Patent
Hospodor et al.

(10) Patent No.: US 9,155,767 B2
(45) Date of Patent: Oct. 13, 2015

(54) ESSENTIAL ELEMENT MANAGEMENT

(71) Applicants: Andrew D. Hospodor, Santa Cruz, CA (US); Robert J. Rapp, San Jose, CA (US)

(72) Inventors: Andrew D. Hospodor, Santa Cruz, CA (US); Robert J. Rapp, San Jose, CA (US)

( * ) Notice: Subject to any disclaimer, the term of this patent is extended or adjusted under 35 U.S.C. 154(b) by 315 days.

(21) Appl. No.: 13/655,410

(22) Filed: Oct. 18, 2012

(65) Prior Publication Data

US 2014/0113010 A1    Apr. 24, 2014

(51) Int. Cl.
*A61K 36/00* (2006.01)
*A61K 36/185* (2006.01)
*B01D 11/02* (2006.01)

(52) U.S. Cl.
CPC .......... *A61K 36/185* (2013.01); *B01D 11/0219* (2013.01); *A61K 2236/39* (2013.01)

(58) Field of Classification Search
None
See application file for complete search history.

(56) References Cited

U.S. PATENT DOCUMENTS 2,397,611 A * 4/1946 Lougovoy et al. ............ 528/482
2005/0165088 A1 * 7/2005 Whittle et al. ................ 514/454

OTHER PUBLICATIONS

Guo et al, The application of ultrasonic in degumming for hemp. Applied Physics Research (2010), 2(1), 139-143.*
Clark, Medical marijuana: medical necessity versus political agenda. Medical science monitor: international medical journal of experimental and clinical research, (Dec. 2011) vol. 17, No. 12, pp. RA249-61.*

* cited by examiner

*Primary Examiner* — Qiuwen Mi
(74) *Attorney, Agent, or Firm* — Robert J. Rapp

(57) ABSTRACT

The invention extends the utility of apparatus used to extract medicinal *cannabis* compounds into an eluate by separating a portion of medicinal *cannabis* compounds contained within a portion of eluate at a first extraction target level providing enough clean solvent to continue extraction operations. A high efficiency concentrator such as a rotary evaporator or a wiped film evaporator processes eluate from one or more tanks or extraction vessels creating clean solvent when extraction targets are met or when clean solvent is exhausted. This manages eluate concentration levels and limits the quantity of concentrated medicinal *cannabis* compounds on site at any moment in time. The invention enables a business model for keeping medicinal *cannabis* compounds within a legal system, and reduces pollution because law enforcement would no longer have to burn large quantities of *cannabis* plant matter.

17 Claims, 4 Drawing Sheets

Figure 1: Mobile Extractor in Semi Cross Section

Figure 2: A Mobile Extractor Mounted on a Truck

ESSENTIAL ELEMENT MANAGEMENT

BACKGROUND OF THE INVENTION

The federal government of the United States as typified by the Drug Enforcement Agency (DEA), Federal Bureau of Investigation (FBI), and Federal Drug Administration (FDA) consider *cannabis* an illegal substance with no medicinal value. In 2009 the DEA confiscated and burned 2980 metric tons (nearly 6.6 million pounds, or 7,000,000 *cannabis* plants) of *cannabis* plants nearly doubling the 1539 metric tons confiscated and burned in 2008. The FY 2012 DEA Performance Budget Congressional Submission indicates that the DEA eradicated 9,000,000 *cannabis* plants in FY 2010 and 2011, and projects 9,500,000 plants (over 4000 metric tons, or 8.8 million pounds) to be eradicated in FY 2013. The burning of millions of *cannabis* plants emits large amounts carbon, dioxin, gasoline vapors, and other pollutants into the environment.

In contrast the medicinal use of *cannabis* has been legalized and regulated in the District of Columbia, and in 17 states. The legalization of medicinal *cannabis* in these municipalities has led to an expansion of a state regulated distribution of *cannabis* flowers, edible medications, and topical medications available to individuals with proper credentials or recommendations. In an effort to lead the way in providing controlled dosage medications certain technologies have been developed that include the extraction of medicinal *cannabis* compounds from raw *cannabis* in large volumes followed by incorporation of controlled dosages of medicinal *cannabis* compounds into edible or topical medications. For example it is now possible to manufacture predominantly non-psychoactive medications derived from *cannabis*. Characteristically different forms of medical *cannabis* compounds can now be studied in ways not possible before.

The most significant driver for growing demand for legalized medicinal *cannabis* are the increasing bodies of research showing tangible benefits to individuals suffering from a plurality of ailments when using medicinal *cannabis*. Furthermore no toxic or overdose effects from the use of *cannabis* have been medically documented.

In past years various mechanisms for extracting essential elements from raw *cannabis* plant material have been researched by professional scientists, until recently the extraction of medicinal compounds from *cannabis* has been limited to small scale extractions by authorized scientists in the academic realm or has been performed clandestinely by individuals operating outside the law. Applicant's related patent application Ser. No. 13/066,585 (currently under Notice of Allowance) and Ser. No. 13/506,010 relate to extracting medicinal *cannabis* compounds in large volumes from *cannabis* plant material. The invention described in this patent application extends the utility of apparatus built consistent with applicant's previous extraction apparatuses.

As of 2012 states with laws regulating the medicinal use of *cannabis* have not implemented or officially sanctioned any strategy designed to manage *cannabis* waste materials (*cannabis* leaves, trim, imperfect bud material, insect infested, or moldy plants). *Cannabis* plants grown by authorized medical marijuana growers produce materials have been dispensed to patients through dispensaries, yet many patients and dispensaries are not interested is *cannabis* leaves, *cannabis* trimmings, or imperfect bud material. Furthermore moldy *cannabis* plant material or insect infested plant material can cause allergic reactions, fungal infections, or have other negative side effects if consumed by people with compromised immune systems. Without effective strategies for capturing medicinal *cannabis* compounds contained within such "waste" *cannabis* plant material poses a risk that these materials may be diverted into gray or black markets or end up in rivers, streams, or in landfills.

The focus of the present invention relates to an improved apparatus, process, and business methods for extracting medicinal elements from *cannabis* plant material and then keeping cannabinoids within a legal system without emitting vast amounts of pollution into the environment.

BRIEF DESCRIPTION OF THE INVENTION

Applicant hereby incorporates by reference his earlier patent application Ser. No. 13/066,585 entitled Essential Element Extractor and Ser. No. 13/506,010 Recycling cannabinoid extractor into this patent application.

Applicant's earlier inventions described in patent application Ser. No. 13/066,585 (Essential Element Extractor) and Ser. No. 13/506,010 (Recycling cannabinoid extractor) describe processes and apparatus used to extract medicinal *cannabis* compounds from *cannabis* plant material and store them in an eluate. Such an eluate contains low concentrations of medicinal *cannabis* compounds per unit volume of solvent is stored in a storage tank or a "dirty tank"; applicant's tank or entire extraction apparatus is also typically configured to be transported on or by a vehicle. After a plurality of extractions applicant's eluate accumulates medicinal *cannabis* compounds creating "dirty" solvent. Eventually clean solvent transported into the field thus becomes dirty. Sufficiently dirty solvent reduces the efficiency of the apparatus because without clean solvent to rinse the *cannabis* plant material after extraction a low density residue of medicinal *cannabis* compounds may be left on the *cannabis* plant matter after extraction. Furthermore repeated extractions using dirty solvent may cause applicant's eluate to exceed targeted concentrations of medicinal *cannabis* compounds per unit volume of solvent.

Applicant's improved invention separates a portion of medical *cannabis* compounds contained in a portion of an eluate creating a more concentrated portion of dirty eluate or a concentrate of medicinal *cannabis* compounds and a portion of clean solvent. To accomplish this, a high efficiency concentrator such as a rotary evaporator (roto-vap) or a wiped film evaporator processes eluate from applicant's dirty tank or eluate output from his extraction vessel or "hopper" as referred to in applicant's earlier patent applications referenced above and incorporated within this disclosure. The invention also includes a business model for managing essential elements contained within *cannabis* by keeping them within a legal system until they are consumed or destroyed. The invention is thus an improved apparatus, process, and a business method.

Applicant's invention enables law enforcement to stop burning *cannabis* plants in the field while allowing operations in the field to continue virtually indefinitely. This eliminates the need for law enforcement to pollute the atmosphere by burning millions of pounds of *cannabis* they confiscate each year.

The invention also allows municipalities with medicinal marijuana laws to enact strategies for recovering medicinal *cannabis* compounds from waste *cannabis* materials and keep them within that states legal system.

Applicant's invention thus eliminates dis-advantages inherent in diametrically opposed theaters of the debate about how *cannabis* should be treated in our society. It provides benefits to those who wish to regulate *cannabis* as a medication and to those who wish to eradicate *cannabis* because it is an illegal substance under Federal law.

DETAILED DESCRIPTION OF THE INVENTION

Applicant hereby incorporates by reference his earlier patent application Ser. No. 13/066,585 entitled Essential Element Extractor and Ser. No. 13/506,010 Recycling cannabinoid extractor into this patent application.

Applicant's earlier inventions described in patent application Ser. No. 13/066,585 (Essential Element Extractor) and Ser. No. 13/506,010 (Recycling cannabinoid extractor) describe processes and apparatus used to extract medicinal *cannabis* compounds from *cannabis* plant material and store them in an eluate. Such an eluate contains low concentrations of medicinal *cannabis* compounds per unit volume of solvent is stored in a storage tank or a "dirty tank"; applicant's "dirty" tank or entire extraction apparatus is also typically configured to be transported on or by a vehicle. After a plurality of extractions applicant's eluate accumulates medicinal *cannabis* compounds creating "dirty" solvent. Eventually all clean solvent transported into the field thus becomes dirty. Sufficiently dirty solvent reduces the efficiency of the apparatus because without clean solvent to rinse the *cannabis* plant material after extraction a low density residue of medicinal *cannabis* compounds may be left on the *cannabis* plant matter after extraction. Furthermore repeated extractions using dirty solvent may cause applicant's eluate to exceed targeted concentrations of medicinal *cannabis* compounds per unit volume of solvent.

Applicant's earlier inventions include an extraction vessel (a "hopper") in controlled fluid communication with one or more solvent tanks; some embodiments include a clean configured to contain clean solvent and a dirty tank configured to contain an eluate of medicinal *cannabis* compounds and solvent.

Applicant's improved invention separates a portion of medical *cannabis* compounds contained in a portion of an eluate creating a more concentrated portion of dirty eluate or a concentrate of medicinal *cannabis* compounds and a portion of clean solvent. To accomplish this, a high efficiency concentrator such as a rotary evaporator (roto-vap) or a wiped film evaporator processes eluate from applicant's dirty tank or eluate output from his extraction vessel or "hopper" as referred to in applicant's earlier patent applications referenced above and incorporated within this disclosure. The invention also includes a business model for managing essential elements contained within *cannabis* by keeping them within a legal system until they are consumed or destroyed. The invention is thus an improved apparatus, process, and a business method.

Applicant's current invention extends the utility and efficiency of applicant's earlier inventions because clean solvent may be produced to continue field operations. Without the ability to create at least a small amount of clean solvent, field operation would have to be paused until additional clean solvent were transported on site.

A high efficiency concentration apparatus is an apparatus capable of quickly concentrating at least a portion of medicinal *cannabis* compounds by separating them from solvent used in previous extractions. Examples of a high efficiency concentration apparatus include a wiped film evaporator or a rotary evaporator (roto-vap), each are evaporative separators. Here again applicant's apparatus or portion of applicant's apparatus are typically configured for transport one or by a vehicle.

After applicant's extraction apparatus completes a plurality of extractions, applicant's dirty tank will contain a "targeted volume of eluate" or an eluate that contains a "targeted concentration level of medicinal *cannabis* compounds per unit volume of solvent".

Applicant hereby defines the term "extraction targets" to mean either a "targeted volume of eluate" or a "targeted concentration level of medicinal cannabinoids per unit volume of solvent".

Applicant also hereby defines "extraction target tiers" as meaning either a set of increasing "targeted volumes of solvent" or a set of increasing "targeted concentration levels of medicinal *cannabis* compounds per unit volume of solvent".

In some embodiments of applicant's invention the total amount of medicinal *cannabis* compounds or the density of medicinal *cannabis* compounds contained in one eluate or in a plurality of eluates can be controlled by using pre-determined regimens.

Applicant's improved invention couples a high efficiency concentration apparatus to his dirty tank and/or to his hopper for use when required or desired. For example the high efficiency concentration apparatus may be used to separate a portion of the medicinal *cannabis* compounds from a portion of dirty solvent. The high efficiency concentration apparatus would have two outputs: 1. a more concentrated eluate or a concentrate of medicinal *cannabis* compounds; 2. clean solvent.

Extraction targets may be set based on various parameters that include yet are not limited to: volumes of eluate, measurements of eluate concentration, or combination thereof. Extraction targets include yet are not limited to: the weight of *cannabis* plant matter extracted within a volume of solvent, the number of plants or portion of plants extracted within a volume of solvent, a measurement of the volumetric density of medicinal *cannabis* compounds contained within applicant's eluate, a visual indication such as the opaqueness of applicant's eluate, and/or measurement of residual medicinal *cannabis* compounds contained within *cannabis* plant matter after extraction.

Applicant's invention also controls eluate concentration density in various ways and may be configured to concentrate desired amounts of eluate to produce a desired amount of clean solvent. Applicant's improved invention allows more raw *cannabis* to be extracted into eluate on an as needed basis. When certain extraction targets are met and more *cannabis* becomes available, controlled amounts of clean solvent may be produced allowing field operations to continue.

For example if a first target concentration density of medicinal *cannabis* compounds is 0.5 milligrams per milliliter of solvent was attained, a concentration protocol could be initiated wherein 25 liters of eluate were separated into 20 liters of clean solvent and 5 liters of more concentrated eluate. The concentration density of medicinal *cannabis* compounds in the more concentrated second eluate would be 2.5 milligrams per milliliter (12.5 milligrams in 5 liters).

The more concentrated eluate then could be a. Mixed back into the dirty tank slightly increasing the concentration density in the dirty tank, b. Stored in a second dirty tank, or c. Concentrated further and cared for under a security protocol.

This process could be repeated until a. A second target concentration density of medicinal *cannabis* compounds is reached in the dirty tank, b. The second dirty tank is full, or c. The concentrate is moved offsite or destroyed as required by a desired security protocol.

Applicant's invention is not limited any specific targeted concentration of eluate as virtually any target concentration of medicinal *cannabis* compounds per unit volume of solvent may be set.

Applicant's process and apparatus scales from smaller (pickup/flatbed truck sized), to medium (semi-truck sized), and to fixed placed stationary factory embodiments Another example of applicant's invention includes a wiped film evaporator connected to a dirty tank or to an extraction vessel such as applicant's "hopper". When an extraction target is met or exceeded a certain amount of eluate can be transferred from applicant's dirty tank and/or applicant's hopper to the wiped film evaporator.

Such a wiped film evaporator configured to separate 75% of solvent from 100 liters of eluate in a single pass would provide 75 liters of clean solvent and 25 liters of a more concentrated eluate. If the initial eluate contained 10 milligrams of medicinal *cannabis* compounds per milliliter of eluate, 100 liters of such an eluate would contain 100 grams of medicinal *cannabis* compounds. The more concentrated eluate would contain 100 grams of medicinal *cannabis* compounds in 25 liters of eluate or 40 milligrams of medicinal *cannabis* compounds per milliliter of eluate after one pass through the wiped film evaporator. If the eluate were cycled through the wiped film evaporator many times additional clean solvent and a concentrate of medicinal *cannabis* compounds would be created.

Applicant's notes that his improved invention also prevents the accumulation of a residue of medicinal *cannabis* compounds on extracted plant matter, because clean solvent would always be available to rinse the *cannabis* plant matter after an extraction.

In certain embodiments applicant's improved invention creates a concentrate of medicinal *cannabis* compounds; the presence of such a concentrate is at higher risk of being stolen than applicant's eluate because it is a highly valued drug substance in a concentrated form. In order to mitigate the possibility of theft security protocols or conventions may be incorporated into the operation of applicant's improved invention.

Security conventions include yet are not limited to a plan, a set of rules, or an apparatus used to protect or destroy the concentrated medicinal *cannabis* compounds.

Examples of security protocols/conventions:
On site law enforcement or authorized personnel that take possession of concentrated medicinal *cannabis* compounds as they are produced.
The destruction of concentrated medicinal *cannabis* compounds on site by authorized personnel, or by law enforcement.
Supervision of all extraction/concentration activities by authorized personnel, or law enforcement.
The immediate incorporation of the concentrated *cannabis* compounds into medicinal products on site.
The secure isolation and transport of concentrated medicinal *cannabis* compounds to a facility where they may be incorporated into medicinal products or destroyed.
Transportation of extractors on separate vehicles from high efficiency concentration apparatuses.
The sequestering of medicinal *cannabis* compounds into elements that cannot be consumed, eaten, or smoked.
The vaporization of medicinal *cannabis* compounds from a concentrate of medicinal *cannabis* compounds.
Obfuscation of the presence of high efficiency concentration apparatuses on a vehicle transporting extraction apparatuses.

Preferred embodiments of the invention are configured to transport applicant's eluate containing a low concentration of medicinal *cannabis* compounds per unit volume of solvent without transporting a concentrate of medicinal *cannabis* compounds on or by the same vehicle as applicant's eluate, extraction apparatus, or highly efficient concentration apparatus. In these embodiments a thief would not have easy access to concentrated medicinal *cannabis* compounds.

Embodiments of the invention where an extraction apparatus is transported on or by a vehicle and a highly efficient concentration apparatus are transported on or by a different vehicle; thieves who stole one apparatus and not the other would not be enabled to perform both extractions and concentrations because they would only have one apparatus and not the other.

Applicant's invention enables law enforcement to stop burning *cannabis* plants in the field while allowing operations in the field to continue virtually indefinitely. This eliminates the need for law enforcement to pollute the atmosphere by burning millions of pounds of *cannabis* they confiscate each year.

The invention also allows municipalities with medicinal marijuana laws to enact strategies for recovering medicinal *cannabis* compounds from waste materials and keep them within that states legal system.

Applicant's invention thus eliminates dis-advantages inherent in diametrically opposed theaters of the debate about how *cannabis* should be treated in our society. It provides benefits to those who wish to regulate *cannabis* as a medication and also to those who wish to eradicate *cannabis* because it is an illegal substance under Federal law.

The invention also enables a new business model that may be operated under the supervision of law enforcement eradicating *cannabis* while minimizing pollution, or under the authorization of state medical marijuana laws.

The business method includes:
The authorized extraction of medicinal *cannabis* compounds from *cannabis* plant matter in the field.
Security by containing low concentrations of medicinal *cannabis* compounds into a volume of solvent.
Secondary security measures that regulate how concentrates are to be handled in the field and/or in a secure processing facility.
Apparatus in such a business model may be operated by the principal who developed the technology on a contractual basis, may be operated by authorized leases, or by licensing the technology to entities regionally.
The apparatus of the invention is not limited to a single extraction system, hopper (extraction vessel), solvent tank, or high efficiency concentrator. The invention may contain a plurality of hoppers, extraction systems, solvent tanks, or high efficiency concentrators. Check valves may also be incorporated into the invention to prevent back flow from one vessel or portion of the apparatus and another. Nonflammable gas may also be introduced into one or more of the vessels in the apparatus and may be used to displace oxygen or be applied under pressure to facilitate fluid flow from one vessel to another. Pressure relief valves may also be used to prevent over pressurization of a tank and be used to vent excess nonflammable gas to the environment or to a solvent vapor trap. A solvent vapor trap may contain a filter such as an activated carbon filter or include a cooled tank or compensator. A preferred nonflammable gas is nitrogen.

Figure 1:
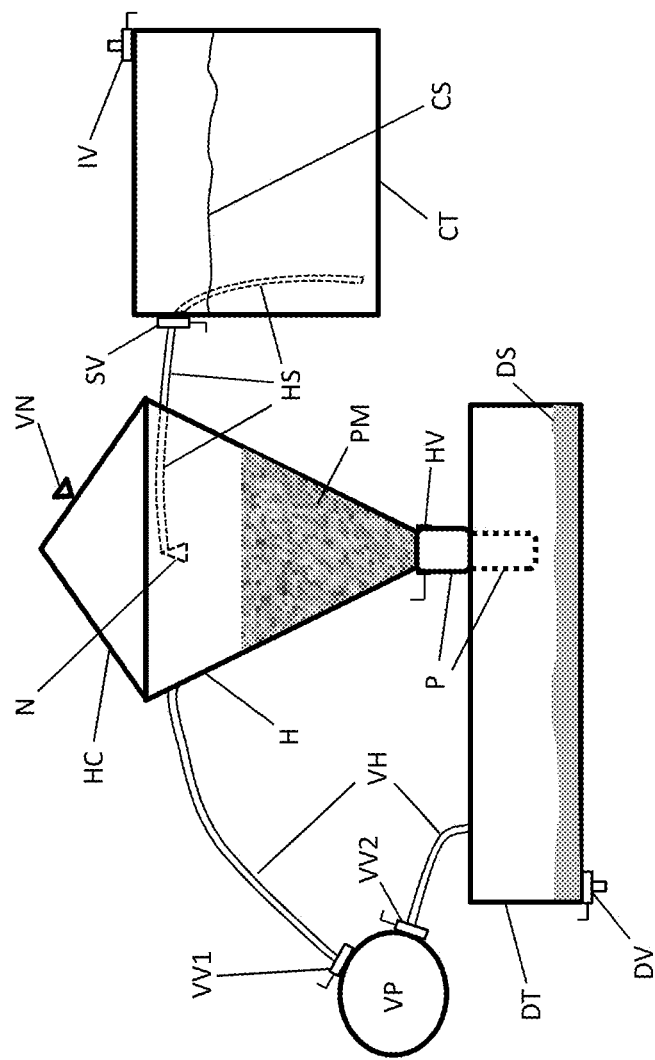
FIG. 1 entitled "Mobile Extractor in Semi Cross Section" shows.

A clean tank CT filled with a clean solvent CS; a hopper H with hopper cover HC is connected to the clean tank CT by a hose HS, portions of the hose HS within the clean tank CT and within the hopper H are shown with dashed lines indicating that a portion of the hose H is inside the hopper H and inside the clean tank CT.

Inside of the hopper H is a nozzle N (shown with dashed lines) and plant material PM is shown in gray. The hopper is connected to a hopper valve HV to the dirty tank DT by a pipe P. When the hopper valve is closed solvent will not flow from the hopper H to the dirty tank DT. The dirty tank is shown containing a portion of dirty solvent DS. The hopper also is depicted as having a vent, item VN.

A solvent valve (fuel or solvent pump) item SV is located on the clean tank and is attached to hose HS, the solvent valve when open will allow clean solvent CS to be sucked into the hopper by the vacuum pump VP. When closed solvent valve SV will block the flow of clean solvent CS from the clean tank to the hopper. Item SV alternatively may be a conventional fuel pump used to pump solvent from the clean tank to the hopper. The solvent valve item SV may alternatively be a pump configured to pump solvent (i.e.: a fuel or solvent pump) that actively pumps solvent from the clean tank to the hopper.

Vacuum hoses connect the vacuum pump VP to the hopper H and to the dirty tank DT. Two separate vacuum valves VV1 and VV2 connect two separate vacuum hoses VVH to the hopper H and to the dirty tank DT respectively. Each valve VV1 and VV2 may be operated independently; they provide vacuum pressure to the mobile extractor as desired. When VV1 is open, the hopper H has a vacuum applied to it, when VV2 is open the dirty tank DT has a vacuum pressure applied to it.

By opening vacuum valve 1 VV1, when vacuum valve 2 VV2 is closed, a vacuum pressure is applied to the hopper H, this causes solvent to be sucked into the hopper from the clean tank CT when the solvent valve SV is open. At this point in time hopper valve HV is typically closed. The vacuum will cause the hopper H to fill with clean solvent CS. This is when the plant material is soaked or washed with clean solvent CS.

Evacuating the hopper: When vacuum valve 1 VV1 is open, when vacuum valve 2 VV2 is closed, when the hopper valve HV is open, and when the solvent valve SV is closed solvent will be sucked and forced by gravity into the dirty tank DT through pipe P; In this state vacuum pressure is applied to the hopper H and the dirty tank DT causing the hopper H to be sucked dry, vent, item VN if opened slightly will allow air to enter the hopper increasing the efficiency of this process. Typically a screen or filter (not depicted) located between the hopper H and the hopper valve HV will prevent plant material PM from falling into the dirty tank DT. A portion of pipe P extending into the dirty tank DT is shown with dashed lines. Applicant's hopper valve HV may be a pump configured to pump solvent (such as a fuel or solvent pump).

Rinsing the plant material: When vacuum valve 1 VV1 is open, when solvent valve SV is open, when hopper valve HV is open clean solvent CS will be sucked from the clean tank CT into the hopper H, through the plant material PM, and into the dirty tank DT; at this point in time vacuum valve 2 will typically be closed, yet if vacuum valve 2 VV2 were open the plant material PM would still be rinsed by the solvent and the solvent would still flow into the dirty tank DT becoming dirty solvent DS. In this state vacuum pressure may be applied to the entire system.

Also connected to the clean tank is input valve IV, this valve is typically closed, yet may be opened to add more clean solvent CS into the clean tank CT.

Another valve, the drain valve DV is connected to the bottom of the dirty tank DT, the drain valve DV is typically closed, yet when open will cause the dirty solvent DS to drain out of the dirty tank DT.

Figure 2:
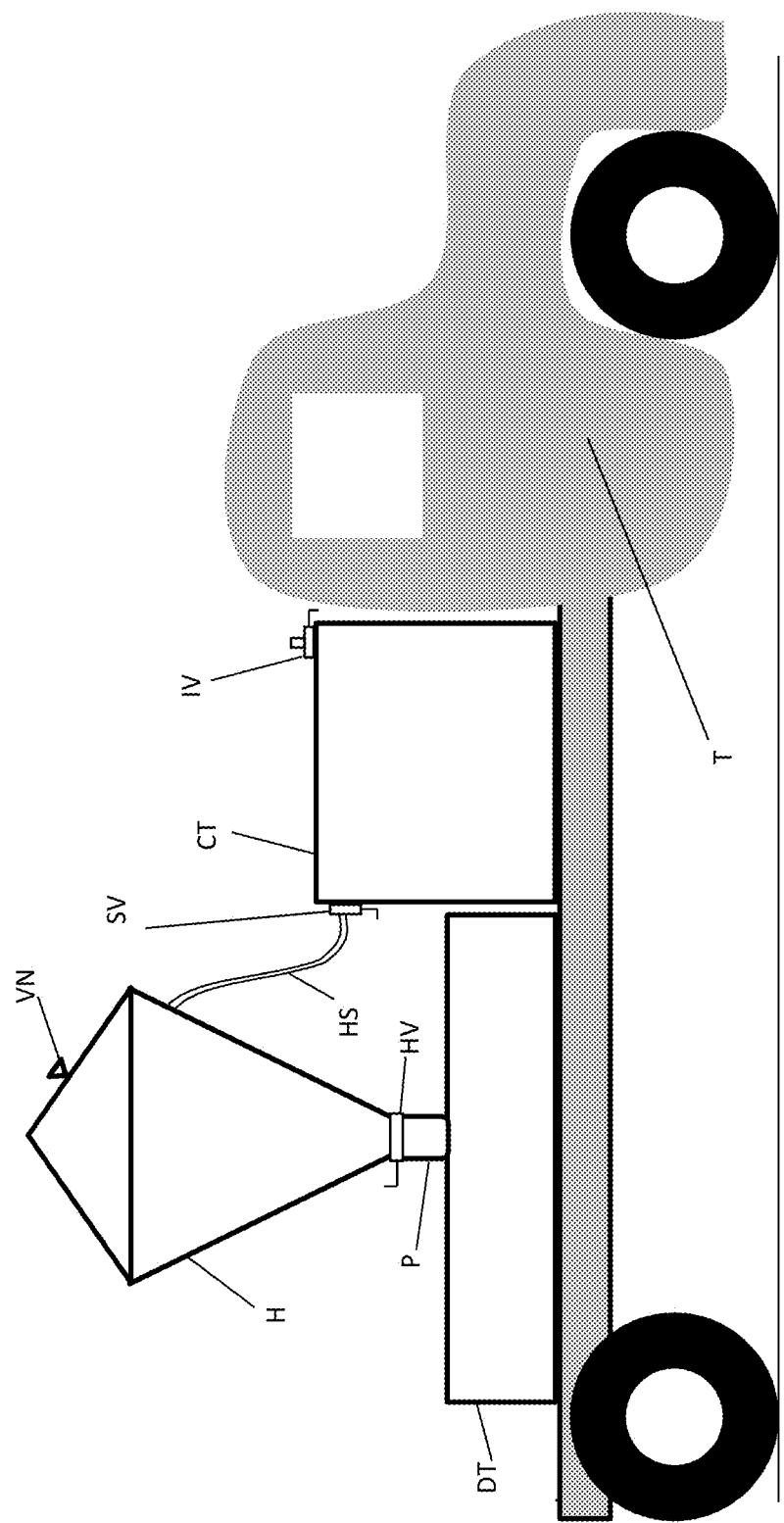

FIG. 2: entitled "A Mobile Extractor Mounted on a Truck" shows:

A truck T on which elements of the mobile extractor are mounted: the clean tank CT with input valve IV and solvent valve SV are depicted.

The solvent valve SV (or pump) is again connected to the hopper H by a hose HS; the hopper H is connected to a hopper valve HV (or pump configured to pump solvent) which in turn is connected to a pipe P and to the dirty tank DT; a vent VN on the hopper is also depicted. For sake of clarity the vacuum pump, vacuum hoses, vacuum valves, and the drain valve that were depicted in FIG. 1 are not shown in FIG. 2.

Figure 3:
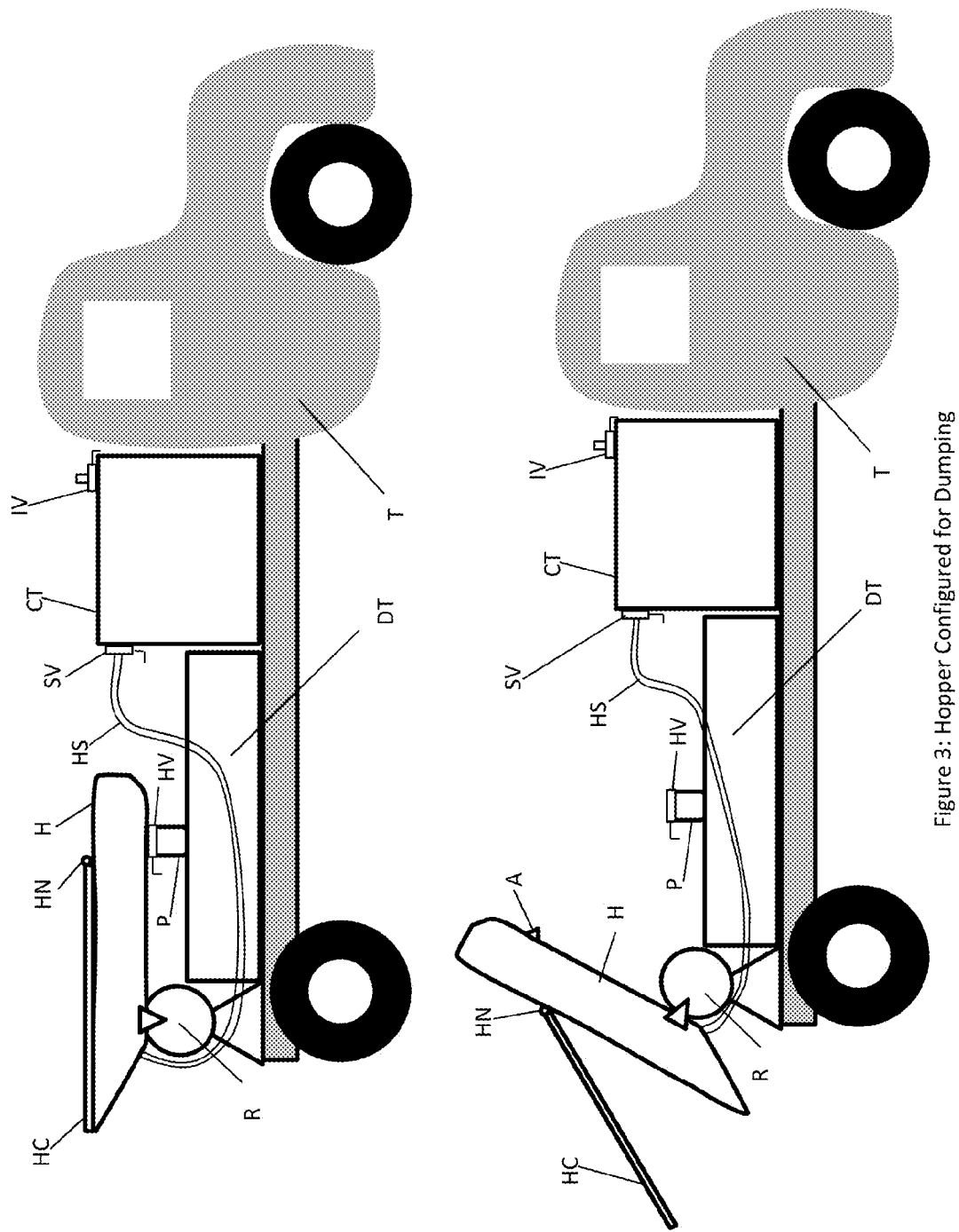

FIG. 3: entitled "Hopper Configured for Dumping" depicts a wheel barrow shaped hopper H on truck T.

The top figure in FIG. 3 shows the hopper H in its working position.

Also depicted are hopper cover HC with a hinge HN, hose HS, solvent valve or fuel pump, item SV, the clean tank CT, the dirty tank DT, a hopper valve (or pump) HV, a pipe P connecting the hopper valve HV to the dirty tank DT, and input valve IV. Item R is a rotational member; it is an apparatus that allows the hopper H to be rotated and dumped. The bottom figure in FIG. 3 shows all of the elements mentioned above (hopper H, hinge HN, hopper cover HC, hose HS, solvent valve or fuel pump SV, clean tank CT, dirty tank DT, hopper valve (or pump) HV, pipe P, input valve IV, and rotational member R) yet shows the hopper H in the dumping configuration where hopper cover HC opens using hinge HN; this allows contents of the hopper H to be dumped. Also depicted is adaptor A, adaptor A allows the hopper to be connected to hopper valve (or pump) HV in a secure way.

Note that hose HS connects to the hopper near the point of rotation R of the hopper H, this allows the hopper H to be dumped without stressing or pulling on the hose HS.

Applicant notes that the apparatus depicted in his FIGS. 1-3 depict embodiments of apparatus consistent with his earlier invention, those inventions are not limited to these embodiments.

Figure 4:
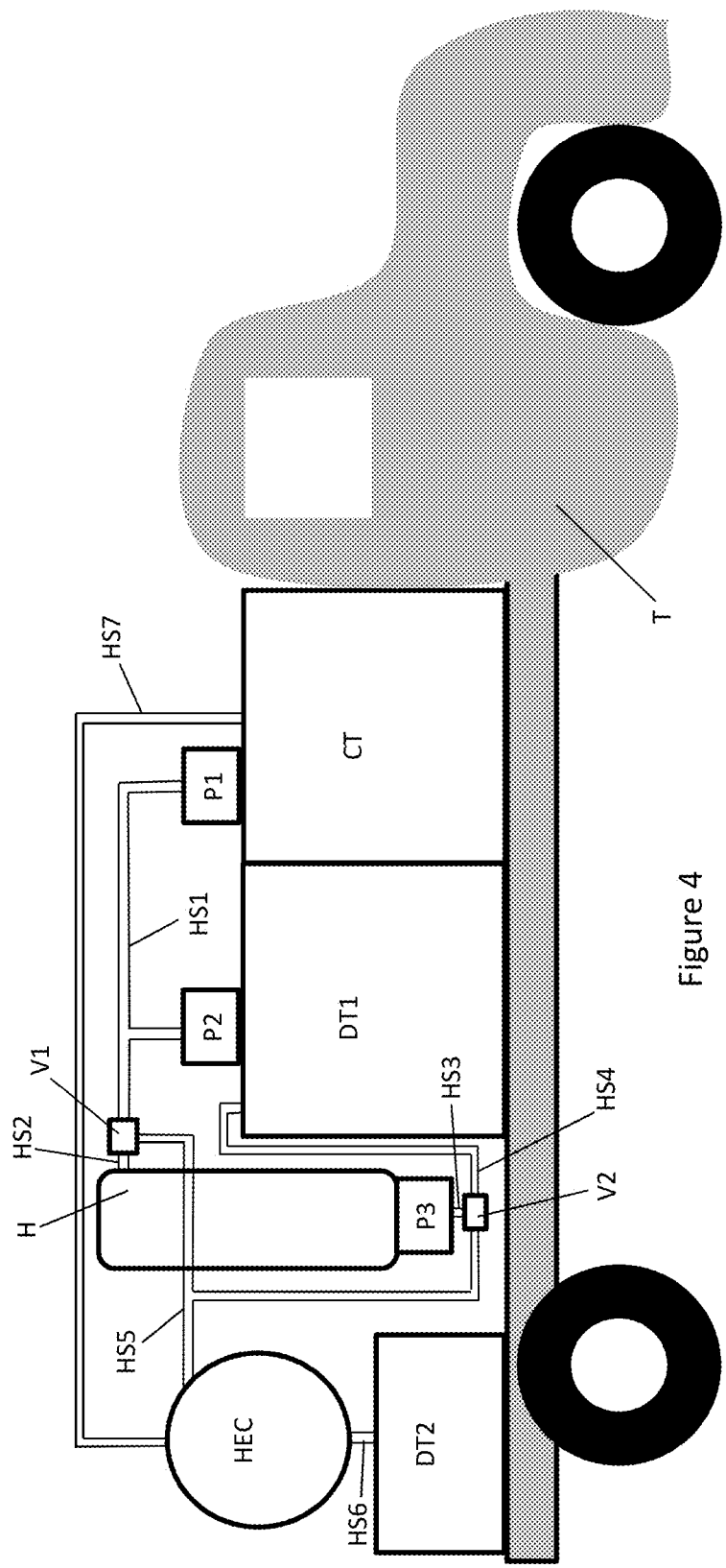

FIG. 4: Applicant's FIG. 4 depicts a truck T containing a clean tank CT, a first dirty tank DT1, a hopper H, pumps P1 P2 and P3, valves V1 and V2, a high efficiency concentrator HEC, a second dirty tank DT2, and hoses (or pipes) HS1 through HS7.

The extraction system includes the clean tank CT, the first dirty tank DT1, the hopper H, pumps P1 P2 and P3.

Valve V1 is configured to switch solvent flow from hose HS1 to the hopper H through valve V1 and hose HS2, or from hose HS1 to the high efficiency concentrator HEC through valve V1 and hose HS5. Valve V1 thus is configured to control whether eluate flows from the first dirty tank DT1 through pump P2 and into the hopper H or into the high efficiency concentrator when pump P2 pumps eluate.

Valve V2 is configured to control solvent flow from the hopper H through hose HS3, valve V2 and into the first dirty tank through hose HS4; or to the high efficiency concentrator HEC through hose HS3, valve V2, and hose HS5.

Hose HS6 is configured to transport an eluate from the high efficiency concentrator to the second dirty tank DT2. Hose HS7 is configured to transport clean solvent output by the high efficiency concentrator HEC to the clean tank.

In this embodiment the high efficiency concentrator HEC can thus separate clean solvent from an eluate sourced from the first dirty tank DT1 or from the hopper H and to create a more concentrated eluate that is stored in the second dirty tank DT2.

The invention claimed is:

1. A process for extracting cannabinoids from *cannabis* plant matter, the process comprising:
   transporting a first cannabinoid containing eluate that includes an mixture of solvent and cannabinoids to an input at a high efficiency concentrator (HEC), wherein the HEC is a wiped film evaporator, and wherein recovered clean solvent is output from a first HEC output at the wiped film evaporator;
   transporting at least a portion of the recovered clean solvent into a hopper that contains *cannabis* plant matter creating a second cannabinoid containing eluate; and
   transporting the second cannabinoid containing eluate to the HEC input.

2. The process of claim 1, further comprising outputting a third cannabinoid containing eluate from a second output of the HEC into a HEC output tank, wherein one or more liquid level sensors sense a liquid level in the HEC output tank, the one or more liquid level sensors in communication with an electronic control system.

3. The process of claim 2, wherein the level in the HEC output tank corresponds to an extraction target.

4. The process of claim 3, wherein the extraction target corresponds to a volume of eluate.

5. The process of claim 3, wherein the extraction target corresponds to a density of extracted *cannabis* plant compounds in a volume of solvent.

6. The process of claim 3, wherein the extraction target corresponds to a weight of *cannabis* plant matter.

7. The process of claim 2, wherein the contents of the HEC output tank is provided to a person authorized by law to transport cannabinoids.

8. The process of claim 7, wherein the authorized person represents a law enforcement agency.

9. The process of claim 1, wherein a volume of the recovered clean solvent output from the HEC corresponds to an extraction target.

10. The process of claim 9, wherein an extraction target corresponds to at least one of a number of plants or a weight of *cannabis* plant matter and a volume of solvent.

11. The process of claim 1, further comprising outputting a cannabinoid containing concentrate from a second output the HEC to a HEC output tank, wherein one or more liquid level sensors sense a liquid level in the HEC output tank, the one or more liquid level sensors in communication with an electronic control system.

12. The process of claim 11, wherein the contents of the first HEC output tank is provided to a person authorized by law to transport cannabinoids.

13. The process of claim 12 wherein the authorized person represents a law enforcement agency.

14. The process of claim 1, wherein the first eluate is transferred from the hopper to the HEC.

15. The process of claim 1, wherein the first eluate is transferred from an eluate tank to the HEC input.

16. The process of claim 1, further comprising transferring the second eluate from the first HEC output tank to the HEC input.

17. The process of claim 1, wherein the hopper and the HEC are transported on one or more vehicles prior to extracting the cannabinoids from the *cannabis* plant matter.

* * * * *